US009260357B2

(12) United States Patent
Yarrison et al.

(10) Patent No.: US 9,260,357 B2
(45) Date of Patent: *Feb. 16, 2016

(54) HYDROCARBON CONVERSION PROCESS

(71) Applicant: ExxonMobil Chemical Patents Inc., Baytown, TX (US)

(72) Inventors: Matthew B. Yarrison, Lexington, KY (US); Alok Srivastava, Houston, TX (US); Roshni Jindal, Bukit Batok (SG); Chee Keong Then, Clementi New Town (SG); Rodney S. Smith, Edinburgh Midlothian (GB)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/397,492

(22) PCT Filed: Jun. 21, 2013

(86) PCT No.: PCT/US2013/047031
§ 371 (c)(1),
(2) Date: Oct. 28, 2014

(87) PCT Pub. No.: WO2014/008008
PCT Pub. Date: Jan. 9, 2014

(65) Prior Publication Data
US 2015/0126699 A1  May 7, 2015

Related U.S. Application Data

(60) Provisional application No. 61/668,557, filed on Jul. 6, 2012.

(30) Foreign Application Priority Data

Aug. 14, 2012  (EP) .................... 12180449

(51) Int. Cl.
*C07C 1/22* (2006.01)
*C07C 2/20* (2006.01)
(Continued)

(52) U.S. Cl.
CPC ... *C07C 2/20* (2013.01); *C07C 1/22* (2013.01); *C07C 1/24* (2013.01); *C07C 2/12* (2013.01);
(Continued)

(58) Field of Classification Search
CPC ............. C07C 1/20; C07C 2/02; C07C 2/04; C07C 2/24; C07C 41/01
USPC ................. 585/320–329, 638, 639, 640, 641; 568/697, 699
See application file for complete search history.

(56) References Cited

U.S. PATENT DOCUMENTS 2,720,547 A  10/1955  Wolff et al.
3,121,124 A  2/1964  Verdol
(Continued)

OTHER PUBLICATIONS

U.S. Appl. No. 61/668,557, filed Jul. 6, 2012, Yarrison et al.

*Primary Examiner* — In Suk Bullock
*Assistant Examiner* — Sharon Pregler

(57) ABSTRACT

The invention relates to methods and equipment for converting $C_{3+}$ olefin to, e.g., one or more of di-$C_{3+}$ olefin, oligomers and polymers of $C_{3+}$ olefin, branched $C_{4+}$-aldehydes, $C_{4+}$-carboxylic acids, and $C_{4+}$ oxygenates. The invention encompasses producing methyl tert-butyl ether and diisobutylene, and converting methyl tert-butyl ether to isobutylene.

25 Claims, 3 Drawing Sheets

(51) Int. Cl.
    *C07C 2/86*     (2006.01)
    *C07C 41/06*     (2006.01)
    *C07C 1/24*     (2006.01)
    *C07C 2/12*     (2006.01)
    *C07C 2/28*     (2006.01)
    *C08F 110/10*     (2006.01)

(52) U.S. Cl.
    CPC . *C07C 2/28* (2013.01); *C07C 2/864* (2013.01); *C07C 41/06* (2013.01); *C08F 110/10* (2013.01); *C07C 2531/10* (2013.01)

(56) References Cited

U.S. PATENT DOCUMENTS

| | | |
|---|---|---|
| 3,170,000 A | 2/1965 | Verdol |
| 3,270,081 A | 8/1966 | Verdol et al. |
| 3,665,048 A | 5/1972 | Grane et al. |
| 3,979,461 A | 9/1976 | Ancillotti et al. |
| 4,219,678 A | 8/1980 | Obenaus et al. |
| 4,307,254 A | 12/1981 | Smith, Jr. |
| 4,978,807 A | 12/1990 | Smith, Jr. |
| 5,446,224 A | 8/1995 | Miracca et al. |
| 6,011,191 A * | 1/2000 | Di Girolamo et al. ........ 585/514 |
| 6,919,016 B2 | 7/2005 | Podrebarac et al. |
| 6,936,742 B2 | 8/2005 | Smith, Jr. |
| 7,473,812 B2 | 1/2009 | Peters et al. |
| 7,732,648 B2 * | 6/2010 | Bakshi .......... 568/697 |
| 7,910,786 B2 | 3/2011 | Winterberg et al. |
| 2004/0006252 A1 * | 1/2004 | Smith, Jr. ............ 585/639 |
| 2011/0118523 A1 * | 5/2011 | Winterberg et al. .......... 585/733 |
| 2014/0012054 A1 | 1/2014 | Yarrison et al. |

* cited by examiner

HYDROCARBON CONVERSION PROCESS

PRIORITY CLAIM TO RELATED APPLICATIONS

This application is a National Stage Application of International Application No. PCT/US2013/47031 filed Jun. 21, 2013, which claims priority to and the benefit of U.S. Provisional Application No. 61/668,557, filed Jul. 6, 2012, U.S. application Ser. No. 13/923,892 filed Jun. 21, 2013, and European Application No. 12180449.6 filed Aug. 14, 2012, the disclosures of which are fully incorporated herein by their reference.

FIELD

The invention relates to a method, system, and apparatus for converting $C_{3+}$ olefin to, e.g., one or more of di-$C_{3+}$ olefin, oligomers and polymers of $C_{3+}$ olefin, branched $C_{4+}$ aldehydes, $C_{4+}$ carboxylic acids, and $C_{4+}$ oxygenates. The invention encompasses producing methyl tert-butyl ether and diisobutylene, and converting the co-produced methyl tert-butyl ether to isobutylene.

BACKGROUND $C_{3+}$ olefins, particularly $C_{3+}$ iso-olefins, can be used to produce many useful products. For example, isobutene can be used to produce polyisobutylene, which in turn is used to produce butyl rubber. Isobutene is generally obtained from a mixture of $C_4$ olefins (e.g., 1-butene, 2-butenes). Separating isobutene from the mixture by distillation is difficult because $C_4$ olefins have similar boiling points at atmospheric pressure ("atmospheric boiling point").

U.S. Pat. Nos. 3,121,124; 3,270,081; 3,170,000; and 4,307,254, disclose methods for overcoming this difficulty, e.g., by (i) converting isobutene into a derivative which can be more easily separated from the remaining hydrocarbons in the mixture and then (ii) converting the isolated derivative back to isobutene. The process can utilize an acidic catalyst, as disclosed in U.S. Pat. Nos. 2,720,547 and 4,219,678. The process can be conducted in a single reactor, or in a plurality of reactors as disclosed in U.S. Pat. No. 3,979,461.

One conventional process, disclosed in U.S. Pat. No. 7,910,786, involves obtaining a $C_4$ olefin fraction from hydrocarbon cracking processes such as steam cracking and catalytic cracking. The patent discloses removing multiple-unsaturated hydrocarbons, mainly butadiene, and then reacting the remaining mixture (identified as raffinate I or hydrogenated cracking $C_4$) with methanol to produce methyl tert-butyl ether ("MTBE") from the mixture's isobutene. The MTBE is then separated from the remainder of the $C_4$ mixture, and converted to isobutene and methanol. U.S. Pat. No. 4,307,254 discloses producing the MTBE in a catalytic distillation reactor. Besides decomposing MTBE to produce isobutene, it is also conventional to utilize MTBE as a blendstock for increasing the oxygenate content of gasoline.

Besides their use for producing MTBE and isobutene, $C_{3+}$ olefins can also be utilized for producing di-$C_{3+}$ olefin, such as diisobutylene, which can be blended into gasoline to increase the gasoline's octane number, as disclosed in U.S. Pat. No. 7,473,812.

In cases where (i) alternative oxygenates, such as ethanol are utilized, in place of MTBE for increasing gasoline oxygenate content, and/or (ii) there is insufficient need for the isobutene produced by MTBE decomposition, it would be desirable to simultaneously produce $C_{4+}$ ether and di-$C_{3+}$ olefin from a $C_{3+}$ olefin mixture. Moreover, it would be desirable to configure such a process so that the relative amounts of the ether and di-$C_{3+}$ olefin could be varied, e.g., to meet isobutylene demand.

SUMMARY OF THE INVENTION

In an embodiment, the invention relates to an olefin upgrading method comprising:
(a) providing a first portion of a first olefin mixture and a first process fluid, the first olefin mixture comprising ≥1.0 wt. % of $C_{3+}$ iso-olefins based on the weight of the first olefin mixture, and the first process fluid comprising ≥10.0 wt. % alcohol based on the weight of the first process fluid;
(b) reacting a first portion of the first olefin mixture and the first process fluid to produce a first reaction mixture, the first reaction mixture comprising ether and di-$C_{3+}$ olefin and having a di-$C_{3+}$ olefin:ether molar ratio ≥1.0;
(c) separating from the first reaction mixture a second olefin mixture and a first product, wherein (A) the second olefin mixture comprises ≥0.1 wt. % of oligomers of order ≥3 of $C_{3+}$ olefins based on the weight of the second olefin mixture and (B) the first product (i) comprises at least a portion of the first reaction mixture's di-$C_{3+}$ olefin and at least a portion of the first reaction product's ether and (ii) has a di-$C_{3+}$ olefin:ether molar ratio ≥1.0;
(d) providing a third olefin mixture and a second process fluid, wherein the third olefin mixture comprises (i) a second portion of the first olefin mixture or a fourth olefin mixture, the fourth olefin mixture comprising ≥1.0 wt. % of $C_{3+}$ iso-olefins based on the weight of the fourth olefin mixture, and (ii) at least a portion of the second olefin mixture, and wherein the second process fluid comprises ≥10.0 wt. % alcohol based on the weight of the second process fluid; and
(e) reacting the third olefin mixture and the second process fluid to produce a second reaction mixture, the second reaction mixture comprising ether and having di-$C_{3+}$ olefin:ether molar ratio <1.0.

In another embodiment, the invention relates to an olefin upgrading method comprising:
(a) (i) providing a first olefin mixture and a first process fluid, the first olefin mixture comprising ≥0.1 wt. % of $C_{3+}$ olefins based on the weight of the first olefin mixture, and the first process fluid comprising ≥10.0 wt. % alcohol based on the weight of the first process fluid, and (ii) dividing the first olefin mixture into first and second portions.
(b) reacting the first portion and the first process fluid in a first reactor to produce a first reaction mixture, the first reaction mixture comprising ether and di-$C_{3+}$ olefins and having a di-$C_{3+}$ olefins:ether molar ratio ≥1.0;
(c) separating from the first reaction mixture a second olefin mixture and a first product, wherein (A) the second olefin mixture comprises at least a portion of any unreacted first olefin mixture present in the first reaction mixture and (B) the first product (i) comprises at least a portion of the first reaction mixture's di-$C_{3+}$ olefin and at least a portion of the first reaction mixture's ether and (ii) has a di-$C_{3+}$ olefin:ether molar ratio ≥1.0;
(d) providing a third olefin mixture and a second process fluid, wherein (i) the third olefin mixture comprises ≥1.0 wt. % of $C_{3+}$ olefin based on the weight of the third olefin mixture, (ii) the third olefin mixture contains the second portion of the first olefin mixture and at least a portion of the second olefin mixture, and the (iii) second process fluid comprises ≥10.0 wt. % alcohol based on the weight of the second process fluid;

(e) reacting the third olefin mixture and the second process fluid in a second reactor to produce a second reaction mixture, the second reaction mixture comprising ether and having a di-$C_{3+}$ olefin:ether molar ratio <1.0; and (f) conducting at least a portion of the second reaction mixture to a third reactor for reacting at least a portion of any unreacted third olefin mixture and at least a portion of any unreacted second process fluid in the presence of the second reaction mixture to produce a third reaction mixture; wherein the third reaction mixture comprises ether and has (i) a di-$C_{3+}$ olefin:ether molar ratio <1.0 and a monoolefin:ether molar ratio <0.10.

DETAILED DESCRIPTION OF THE INVENTION

Figure 1:
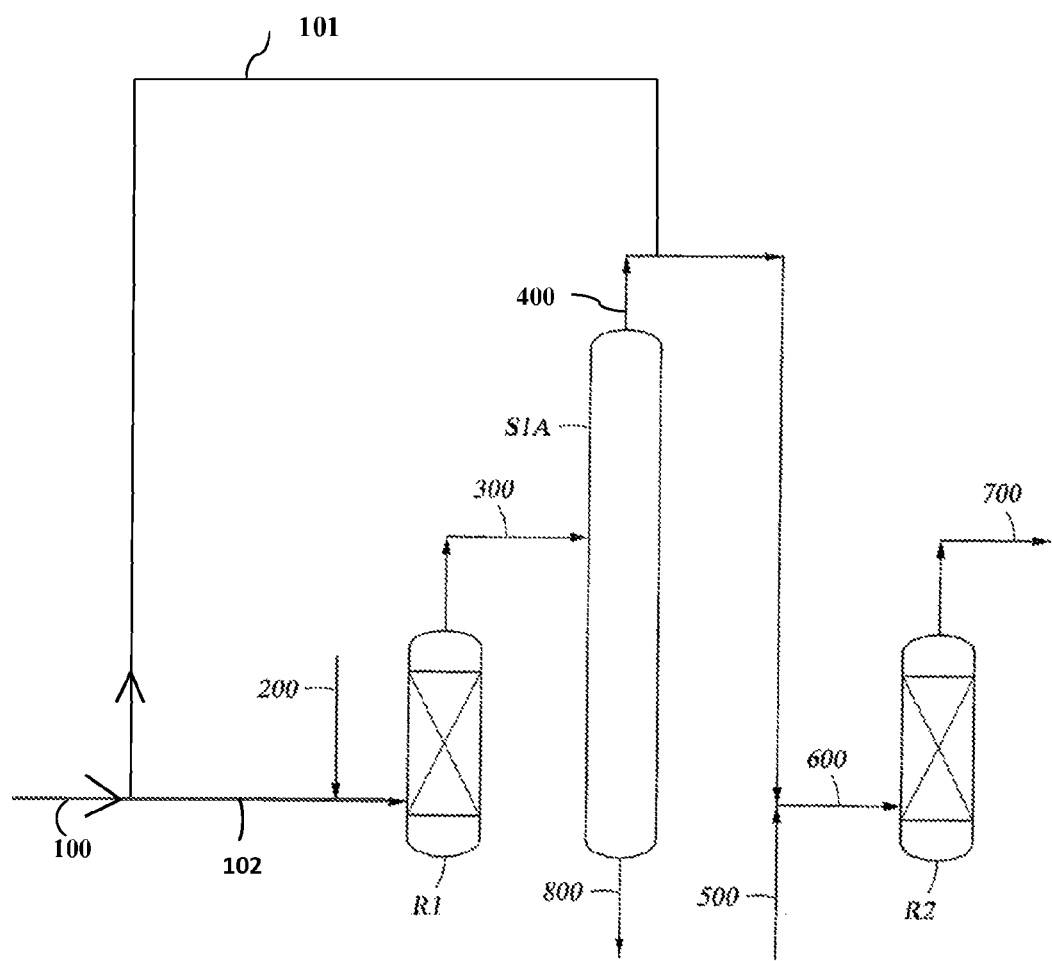
FIG. 1 schematically illustrates a process for converting a feed comprising mixed $C_{3+}$ hydrocarbons (e.g. propylene, propane, butane, isobutene, 2-butenes) in a first reactor to produce a first reaction mixture comprising mono-unsaturated oligomers of order 2 of $C_{3+}$ olefins. A portion of the first reaction mixture is converted to oxygenates in a second reactor.

The invention is based in part on the development of a process and apparatus for simultaneously producing mono-unsaturated oligomers of order 2 of $C_{3+}$ olefins ("di-$C_{3+}$ olefins") and $C_{4+}$ oxygenate from a feed comprising $C_{3+}$ olefin, and optionally decomposing at least a portion of the oxygenate to produce $C_{4+}$ iso-olefin. The process can be operated to produce di-$C_{3+}$ olefins and C4+ oxygenate (e.g., diisobutene and MTBE) in a broad molar ratio range, such as from about 0.01 to about 100, or from about 0.1 to about 10 (di-$C_{3+}$ olefin:$C_{4+}$ oxygenate). It has been observed that the relative commercial demand for di-$C_{3+}$ olefin, $C_{4+}$ oxygenate, and (optionally) $C_{4+}$ iso-olefin can vary significantly in response to gasoline blendstock octane requirements, which are filled by components such as diisobutylene and MTBE and isobutylene demand for producing butyl rubber or for spot commodity markets. The invention fulfills the need for adjusting the product ratios by providing an operator of a $C_{3+}$ olefin conversion processes the flexibility needed to regulate the relative amounts of these species on a demand-driven basis. The exact composition of olefins in the olefin-containing feed (a first olefin mixture) is not critical, and can comprise, e.g., ≥1.0 wt. % of $C_{3+}$ monoolefins (including normal and iso-monoolefin) based on the weight of the first olefin mixture, but it is generally desirable that the amount of polyunsaturated hydrocarbon (e.g., butadiene) be ≤1.0 wt. % based on the weight of the first olefin mixture. For example, the first olefin mixture can comprise ≥1.0 wt. % of $C_{3+}$ iso-olefin based on the weight of the first olefin mixture, e.g., ≥10.0 wt. %, such as ≥20.0 wt. %; and can have a $C_{3+}$ iso-olefin:total $C_{3+}$ hydrocarbon mass ratio ≥0.01, e.g., in the range of 0.10 to 0.30.

A representative first olefin mixture comprising 1- and 2-butenes with isobutene will now be described in more detail. The invention is not limited to this embodiment, and this description is not intended to foreclose other embodiments within the broader scope of the invention.

Representative First Olefin Mixture

In certain embodiments, the first olefin mixture comprises monoolefin, such as ≥1.0 wt. % of $C_{3+}$ monoolefins based on the weight of the first olefin mixture, e.g., ≥1.0 wt. % of $C_{4+}$ iso-olefins, such as ≥1.0 wt. % isobutene. For example, the first olefin mixture can comprise ≥50.0 wt. % of $C_4$ monoolefins based on the weight of the first olefin mixture, such as ≥90.0 wt. % of $C_4$ monoolefins. The $C_4$ monoolefins of the first olefin mixture are generally a mixture of 1-butene, 2-butenes, and isobutene, and the relative amounts of these components can vary. For example, the $C_4$ monoolefins in the first mixture can comprise ≥1.0 wt. % of 1-butene, such as in the range of from 1.0 wt. % to 40.0 wt. %; ≥2.0 wt. % of 2-butenes, such as in the range of from 2.0 wt. % to 45.0 wt. %; and ≥1.0 wt. % of isobutene, such as in the range of 1.0 wt. % to 30.0 wt. %, the weight percent of each species is based on the weight of the first olefin mixture's $C_4$ monoolefins. Besides $C_4$ monoolefins, the first olefin mixture can contain other hydrocarbon species such as propane, n-butane, isobutane, pentane or hexane. Light oxygenate species such as methanol or dimethylether ("DME") may also be present in amounts ≤1.0 wt. %. In one embodiment, the first olefin mixture comprises ≥20.0 wt. % normal butenes, and ≥20.0 wt. % isobutene, and optionally further comprises ≤5.0 wt. % propane, ≤15.0 wt. % n-butane, ≤25.0 wt. % isobutane, ≤1.0 wt. % pentane.

The first olefin mixture can be obtained from one or more source materials. Such source materials can be produced by catalytic cracking, e.g., hydrocracking and/or fluidized catalytic cracking of hydrocarbon feedstocks; and/or by hydrocarbon pyrolysis. At least first and second portions are separated from the first olefin mixture, the first portion being utilized for producing the first reaction mixtures and the second portion being utilized to produce the second reaction mixture. The first and second portions are generally of substantially the same compositions. The first and second portions can be separated from the first olefin mixture using e.g., valve means, dividing means, etc. One embodiment for producing the source material will now be described in more detail. The invention is not limited to this method for producing the source material, and the description is not meant to foreclose other methods for producing the source material within the broader scope of the invention.

Obtaining a Source Material by Pyrolysis

In certain embodiments, the source material is produced by steam cracking of a feed comprising hydrocarbon and water (steam). One conventional steam cracking process utilizes a pyrolysis furnace which has two main sections: a convection section and a radiant section. The feed typically enters the convection section of the furnace, where the feed's hydrocarbon component is heated and vaporized by indirect contact with hot flue gas from the radiant section and by direct contact with the feed's steam component. The steam-vaporized hydrocarbon mixture is then introduced into the radiant section where the cracking takes place. A steam-cracker product is conducted away from the pyrolysis furnace, the steam-cracker product comprising a mixture of products resulting from the pyrolysis of the feed (generally products of hydrocarbon pyrolysis) and unreacted components of the feed (primarily water). At least one separation stage is generally located downstream of the pyrolysis furnace, the separation stage being utilized for separating from the steam-cracker product one or more of light olefin, steam cracker naphtha, steam cracker gas oil, separation stage bottoms (e.g., primary fractionator bottoms), steam cracker tar, steam cracker coke, water, unreacted hydrocarbon components of the feed, etc. The separation stage can comprise, e.g., a primary fractionator. Optionally, a cooling stage is located between the pyrolysis furnace and the separation stage.

The steam cracker feed can be produced by combining the hydrocarbon with a diluent comprising steam, e.g., at a ratio of 0.2 to 4.0 kg steam per kg hydrocarbon. For example, feed's hydrocarbon component can comprise ≥10.0 wt. %, e.g., ≥50.0 wt. %, such as ≥90.0 wt. % (based on the weight of the hydrocarbon component) of one or more of naphtha, gas oil, vacuum gas oil, crude oil, resid, or resid admixtures; including those comprising ≥about 0.1 wt. % asphaltenes. Suitable crude oils include, e.g., high-sulfur virgin crude oils, such as those rich in polycyclic aromatics.

When a heavy hydrocarbon feed, e.g., crude oil or fractions thereof, it can be desirable for the pyrolysis furnace to utilize at least one vapor/liquid separation device (sometimes referred to as flash pot or flash drum) integrated therewith. Such vapor/liquid separator devices are particularly suitable when the feed's hydrocarbon component comprises ≥about 0.1 wt. % asphaltenes based on the weight of the feed's hydrocarbon component, e.g., ≥about 5.0 wt. %.

The vapor/liquid separation device can be used to separate and conduct away at least a portion of the feed's high molecular-weight molecules, such as asphaltenes. Conventional vapor/liquid separation devices can be utilized, though the invention is not limited thereto. Examples of such conventional vapor/liquid separation devices include those disclosed in U.S. Pat. Nos. 7,138,047; 7,090,765; 7,097,758; 7,820,035; 7,311,746; 7,220,887; 7,244,871; 7,247,765; 7,351,872; 7,297,833; 7,488,459; 7,312,371; and 7,235,705, which are incorporated by reference herein in their entirety. Suitable vapor/liquid separation devices are also disclosed in U.S. Pat. Nos. 6,632,351 and 7,578,929, which are incorporated by reference herein in their entirety.

Suitable steam cracking conditions include, e.g., exposing the feed to a temperature (measured at the radiant outlet) ≥400° C., e.g., in the range of 400° C. to 900° C., and a pressure ≥0.1 bar, for a cracking residence time period in the range of from about 0.01 second to 5.0 seconds. When the steam cracker feed comprises heavy hydrocarbon and 10.0 wt. % to 90.0 wt. % water based on the weight of the feed, the steam cracking conditions generally include one or more of (i) a temperature in the range of 760° C. to 880° C.; (ii) a pressure in the range of from 1.0 bar (absolute) to 5.0 bar (absolute); or (iii) a residence time in the range of from 0.10 seconds to 2.0 seconds. When the specified pyrolysis conditions are utilized, the steam-cracker product generally comprises ≥1.0 wt. % of $C_2$ to $C_4$ unsaturates (light olefin), steam cracker naphtha, and steam cracker gas oil; the relative amount of each of these generally depending on, e.g., the steam cracker's composition, pyrolysis furnace configuration, process conditions during the pyrolysis, etc. The steam-cracker product is conducted away for the pyrolysis section, e.g., for cooling and/or separation stages.

A separation stage is generally utilized downstream of the pyrolysis furnace (and optionally downstream of a cooling stage) for separating from the steam-cracker product one or more of light olefin, steam cracker naphtha, steam cracker gas oil, or water. Conventional separation equipment can be utilized in the separation stage, e.g., one or more flash drums, fractionators, water-quench towers, indirect condensers, etc., such as those described in U.S. Pat. No. 8,083,931.

The source material is generally separated from the steam-cracker product in the separation stage, e.g., separated from the light olefin portion of the steam-cracker product. For example, a de-butanizer can be utilized for separating a $C_4$ stream from the steam-cracker product. The source material can be obtained from the $C_4$ stream by extraction utilizing an extractant (e.g., a mixture of sodium hydroxide and water), with the source material generally comprising at least a portion of the raffinate. Conventional de-butanizing and extracting technology can be used, though the invention is not limited thereto. It is generally desirable for the source material and first olefin mixture to contain ≤1.0 wt. % multi-unsaturated olefin such as butadiene (based on the weight of the source material or the first olefin mixture as the case may be), e.g., ≤0.5 wt. %. Conventional methods can be utilized to do this, but the invention is not limited thereto. Suitable methods include those disclosed in U.S. Pat. No. 7,473,812, which is incorporated by reference herein in its entirety.

When the source material is obtained from a steam-cracker product produced from a heavy hydrocarbon feed under the specified conditions, the source material can comprise, e.g., ≥10.0 wt. % isobutene and ≥25.0 wt. % normal butenes with ≤10.0 wt. % n-butane and $C_{5+}$ material. For example, the source material can comprise 18.0 wt. % to 25.0 wt. % of isobutene and 55.0 wt. % to 65.0 wt. % normal butenes. In certain embodiments, the first olefin mixture comprises at least a portion of the source material. The first olefin mixture (and the fourth olefin mixture, when used) can have substantially the same composition as the source material, such as when the first olefin mixture is derived from the source material by separation (e.g., absorption, distillation, or other physiochemical means) or by dividing the source material into a first portion to be utilized as the first olefin mixture and at least a second portion. This can be done using conventional means (e.g., valves, one or more splitters, etc.). In certain embodiments the fourth olefin mixture is obtained from the same source material as is the first olefin mixture. In certain embodiments utilizing the fourth olefin mixture, the fourth olefin mixture can comprise, e.g., ≥1.0 wt. % of $C_{3+}$ iso-olefin based on the weight of the fourth olefin mixture, e.g., ≥10.0 wt. %, such as ≥20.0 wt. %; and can have a $C_{3+}$ iso-olefin:total $C_{3+}$ hydrocarbon mass ratio ≥0.01, e.g., in the range of 0.10 to 0.30. The third olefin mixture reacts with a second process fluid in the second reactor to produce a second reaction mixture, the second reaction mixture comprising ether and having di-$C_{3+}$ olefin:ether molar ratio <1.0.

One representative source material comprises a $C_4$ olefin stream obtained by (a) steam cracking a heavy oil, followed by (b) primary fractionation of the steam-cracker product to separate a $C_{3+}$ olefin-containing fraction, (c) depropanizing and depentanizing the $C_{3+}$ olefin-containing fraction, and then separating a raffinate comprising the $C_4$ olefin source material. For example, the source material (and the first olefin mixture) can have the following composition: ≤1.0 wt. % of multi-unsaturated olefin such as butadiene, ≤0.1 wt. % methane, e.g., in the range of 0.01 to 0.1 wt. %; ≤0.1 wt. % propane, e.g., in the range of 0.01 to 0.1 wt. %; ≤2.0 wt. % isobutane, e.g., in the range of 0.5 wt. % to 2.0 wt. %; ≥10.0 wt. % isobutene, e.g., in the range of 15.0 wt. % to 25.0 wt. %; ≥25.0 wt. % 1-butene, e.g., in the range of 30.0 wt. % to 40.0 wt. %; ≥15.0 wt. % T-2-butene, e.g., in the range of 20.0 wt. % to 30.0 wt. %; ≥1.0 wt. % C-2-butene, e.g., in the range of 2.0 wt. % to 10.0 wt. %; and ≤10.0 wt. % n-butane, e.g., in the range of 2.0 wt. % to 10.0 wt. %, the weight percents being based on the weight of the source material or first olefin mixture as the case may be. In embodiments where a fourth olefin mixture is used, the fourth olefin mixture can have a composition that is also within these compositional ranges.

In certain embodiments, a first portion of the first olefin mixture and a first process fluid are conducted to a first reactor where the first olefin mixture and the first process fluid are reacted to produce a first reaction mixture, the first reaction mixture comprising ether and di-$C_{3+}$ olefin and having a di-$C_{3+}$ olefin:ether molar ratio ≥1.0. A first product and a second olefin mixture are separated from the first reaction mixture. The first product comprises ether and at least a portion of the first reaction mixture's di-$C_{3+}$ olefin, and has a di-$C_{3+}$ olefin: ether molar ratio ≥1.0. The second olefin mixture generally comprises at least a portion (e.g., ≥50.0% or ≥75.0% by weight) of any $C_{3+}$ olefin of the first portion of the first olefin mixture that is not reacted in the first reactor. A third olefin mixture, comprising (i) at least a portion of the second olefin mixture and (ii) the second portion of the first olefin mixture is conducted to a second reactor. The third olefin mixture reacts with a second process fluid in the second reactor to produce a second reaction mixture, the second reaction mixture comprising ether and having di-$C_{3+}$ olefin: ether molar ratio <1.0.

Certain embodiments for producing the first and second reaction mixtures and the first product, illustrated in FIG. 1, will now be described in more detail. The invention is not limited to these embodiments, and this description is not meant to foreclose other embodiments within the broader scope of the invention.

Representative Embodiments

As shown in FIG. 1, a first portion 102 of the first olefin mixture 100 is combined with a first process fluid 200 and conducted to first reactor R1 for producing the first reaction mixture 300. The first portion of the first olefin mixture can be any of those specified in the preceding sections. The first portion of the first olefin mixture can be combined with the first process fluid, these being conducted to R1 together as shown. Alternatively, the first portion and first process fluid can be conducted to R1 via separate conduits, i.e., one or more conduits 102 dedicated to conducting the first portion of the first olefin mixture and one or more conduits 200 dedicated to conducting the first process fluid.

The first process fluid generally comprises ≥10.0 wt. % alcohol based on the weight of the first process fluid. The alcohol can be one or more of the alkyl alcohols, such as ethanol and/or methanol. For example, the first process fluid can comprise ≥50.0 wt. % methanol based on the weight of the first process fluid, such as ≥65.0 wt. % methanol. Since it is desired to produce a first product having a di-$C_{3+}$ olefin: ether molar ratio ≥1.0, it is generally desirable to react a significantly larger amount of $C_{3+}$ olefin in the first reactor compared with the amount or alcohol in order to suppress ether formation. When the first reactor produces oligomers of order ≥2 of one or more designated $C_{3+}$ monoolefin in the first olefin mixture, the molar ratio of designated $C_{3+}$ monoolefin: alcohol is generally in the range of 0.10 to 2.0, e.g., 0.10 to 1.5. When (i) the first olefin mixture is a $C_4$ raffinate (e.g., a raffinate I as defined as U.S. Pat. No. 7,473,812) produced by steam cracking a heavy oil, as specified in the preceding sections, and (ii) the first process fluid comprises ≥65.0 wt. % methanol, based on the weight of the first process fluid, the weight ratio of first portion of the first olefin mixture:first process fluid in the first reactor can be, e.g., in the range of $1.0 \times 10^2$ to $1.0 \times 10^3$, e.g., $3.0 \times 10^2$ to $6.0 \times 10^2$, such as $4.0 \times 10^2$ to $5.5 \times 10^2$.

First reactor R1 is utilized for reacting the first portion of the first olefin mixture and the first process fluid to produce the first reaction mixture. In certain embodiments, the first portion and the first process fluid react in the presence of a catalytically effective amount of a first catalyst, R1 being operated under catalytic conversion conditions. Conventional olefin conversion catalysts and conversion conditions can be utilized, though the invention is not limited thereto. Suitable catalysts and catalytic conversion conditions are disclosed, e.g., in U.S. Pat. Nos. 4,219,678; 4,307,254; and 2,720,547, each being incorporated by reference herein in their entirety. Catalysts comprising one or more perflurosulfonic acid resins can be utilized in R1, including those which are copolymers of sulfonyl fluorovinyl ethyl and fluorocarbon. Examples of such catalysts are disclosed in "Innovation", DuPont, Volume 4, No. 3, Spring 1973, and U.S. Pat. Nos. 3,784,399; 3,770, 567; and 3,849,243, which are incorporated by reference herein in their entirety.

In certain embodiments, the catalyst utilized in R1 includes at least one cation exchanger containing one or more sulfonic acid groups, the cation exchanger being, e.g., in the form of a cation exchange resin. Such catalysts can be produced by polymerization or copolymerization of aromatic vinyl compounds followed by sulfonation. Suitable vinyl compounds include, e.g., styrene, vinyl toluene, vinyl naphthalene, vinyl ethylbenzene, methyl sytrene, vinyl chlorobenzene and vinyl xylene. Although the invention is not limited thereto, conventional methods can be utilized for producing the polymers, e.g., polymerization alone or in admixture with other monovinyl compounds, or by crosslinking with polyvinyl compounds such as one or more of divinyl benzene, divinyl toluene, divinylphenylether, etc. Conventional methods are suitable for introducing sulfonic acid groups into the vinyl aromatic polymers, such as those disclosed in U.S. Pat. No. 4,307,254 and in references cited therein. In certain embodiments, the catalyst comprises ≥50.0 wt. % of Amberlyst™-3 (available from Rohm and Haas, Philadelphia, Pa.), e.g., ≥75.0 wt. %, such as ≥95.0 wt. % based on the weight of the catalyst.

Suitable catalytic conversion conditions for R1 include exposing the catalyst, first portion of the first olefin mixture, and first process fluid to a temperature ≥50.0° C., at a pressure ≥1.0 bar (absolute), and a space velocity (LHSV) ≥1. When at least one bed of cation exchange resin catalyst is used in R1, the conditions can include (i) an inlet temperature ≥50.0° C., e.g., in the range of 55.0° C. to 65.0° C. (SOR), rising to an inlet temperature in the range of 75.0° C. to 85.0° C. (EOR); (ii) an outlet temperature ≥65.0° C., e.g., in the range of 65.0° C. to 75.0° C. (SOR), rising to an outlet temperature in the range of 80.0° C. to 90.0° C. (EOR); (iii) a pressure ≥1.0 bar (absolute), e.g., in the range of 10 bar to 20 bar, and (iv) a space velocity (LHSV) in the range of 1 to 7.

The reaction of at least a portion of the $C_{3+}$ olefin of the first portion of the first olefin mixture with at least a portion of the alcohol of the first process fluid under the specified conditions produces a first reaction mixture comprising ether and mono-unsaturated oligomer of order ≥2 such as di-$C_{3+}$ olefin (e.g., diisobutene) and having a di-$C_{3+}$ olefin:ether molar ratio ≥1.0. The first reaction mixture generally further comprises unreacted alcohol, unreacted $C_{3+}$ monoolefin, and oligomers of order ≥3 of $C_{3+}$ olefins. When (i) the first process fluid comprises ≥90.0 wt. % methanol based on the weight of the first process fluid and (ii) the first portion of the first olefin mixture comprises ≥95.0 wt. % of $C_4$ monoolefins based on the weight of the first portion of the first olefin mixture, the first reaction mixture can comprise, e.g., ≤1.0 wt. % methanol; ≤10.0 wt. % isobutene; ≥50.0 wt. % normal butenes; ≤10.0 wt. % MTBE; ≤5.0 wt. % methyl sec-butyl ether ("MSBE"); ≤5.0 wt. % oligomers of order ≥3 of $C_{3+}$ olefin; and ≥10.0 wt. % diisobutene, wherein the diisobutene:ether molar ratio is ≥1.01, such as ≥1.10, or ≥1.20; the weight percents being based on the weight of the first reaction mixture. For example, the first reaction mixture can comprise 0.05 wt. % to 0.5 wt. % methanol; 1.0 wt. % to 10.0 wt. % isobutene; 60.0 wt. % to 80.0 wt. % normal butenes; 2.0 wt. % to 10.0 wt. % MTBE; 1.0 wt. % to 5.0 wt. % MSBE; 1.0 wt. % to 5.0 wt. % oligomers of order ≥3 of $C_{3+}$ olefin; and 10.0 wt. % to 20.0 wt. % diisobutene; the diisobutene:MTBE molar ratio being ≥1.0, such as ≥1.5, e.g., ≥1.8 or ≥2.0. Referring again to FIG. 1, the first reaction mixture is conducted away from R1 via one or more conduits 300 to separation stage S1A, which comprises one or more separators for separating from the first reaction mixture a second olefin mixture and a first product, the first product (i) comprising at least a portion of the first reaction mixture's di-$C_{3+}$ olefin and ether and (ii) having a di-$C_{3+}$ olefin: ether molar ratio ≥1.0. Stage S1A can utilize conventional separation technology, such as one or more fractionators, though the invention is not limited thereto. When stage S1A includes fractional distillation, the first product can comprise, e.g., ≥20.0 wt. % of the first reaction mixture (such as ≥50.0 wt. %) and the second olefin mixture can comprise, e.g., ≤80.0 wt. % of the first reaction mixture, based on the weight of the first reaction mixture. It is observed that the presence of MTBE in R1 (such as when at least a portion of the MTBE obtained from one or more of the first product, the product of R2, or the product of R3 is conducted to R1), can lessen the amount of oligomers of order ≥3 of $C_{3+}$ olefin produced in R1 by shifting chemical equilibrium in favor of di-$C_{3+}$ olefin production.

The first product, which generally comprises ≥50.0 wt. % of the first reaction mixture's di-$C_{3+}$ olefin and ether based on the weight of the first reaction product's di-$C_{3+}$ olefin and ether, e.g., ≥75.0 wt. %, such as ≥90.0 wt. %, can be conducted away from S1A for, e.g., storage, blending with gasoline for improving the gasoline's octane number and/or oxygenate content, or further processing. The first product generally further comprises (a) ≥50.0 wt. % of the first reaction mixture's oligomers of order ≥3 of $C_{3+}$ olefin based on the weight of the first reaction mixture's oligomers of order ≥3 of $C_{3+}$ olefin, e.g., ≥75.0 wt. %, such as ≥90.0 wt. %; and/or (b) ≤50.0 wt. % of the first reaction mixture's methanol based on the weight of the first reaction mixture's methanol, e.g., ≤40.0 wt. %, such as ≤35.0 wt. %. The first product can be conducted away from S1A via one or more conduits 800, for example. The second olefin mixture generally comprises ≥50.0 wt. % of the first reaction mixture's normal $C_{3+}$ monoolefin and iso-$C_{3+}$ monoolefin, based on the weight of the first reaction product's normal $C_{3+}$ olefin and iso-$C_{3+}$ iso-olefin, e.g., ≥75.0 wt. %, such as ≥90.0 wt. %. When (i) the first process fluid comprises ≥90.0 wt. % methanol based on the weight of the first process fluid, (ii) the first olefin mixture comprises ≥95.0 wt. % of $C_4$ monoolefins based on the weight of the first olefin mixture (e.g., the first olefin mixture is a $C_4$ raffinate as specified in the preceding section), and (iii) the first product and the second olefin mixture are separated from the first reaction mixture by fractional distillation, the first product can comprise, e.g., ≤0.5 wt. % methanol, ≤0.1 wt. % isobutene, ≤0.1 wt. % normal butenes, ≤35.0 wt. % MTBE, ≤20.0 wt. % MSBE, ≤10.0 wt. % oligomers of order ≥3 of $C_{3+}$ olefin, and ≥40.0 wt. % diisobutene, wherein the diisobutene: ether molar ratio is ≥1.01, such as ≥1.10, or ≥1.20; the weight percents being based on the weight of the first product. For example, the first product can comprise 0.1 wt. % to 0.2 wt. % methanol; ≤0.1 wt. % isobutene; ≤0.1 wt. % normal butenes; 20.0 wt. % to 30.0 wt. % MTBE; 10.0 wt. % to 20.0 wt. % MSBE; 1.0 wt. % to 10.0 wt. % oligomers of order ≥3 of $C_{3+}$ olefin; and 50.0 wt. % to 60.0 wt. % diisobutene, the diisobutene:MTBE molar ratio being ≥1.5, such as ≥1.8, e.g., ≥2.0. Under these conditions, the second olefin mixture can comprise, e.g., ≤2.0 wt. % methanol; ≥25.0 wt. % isobutene; and ≥50.0 wt. % normal butenes, the weight percents being based on the weight of the second olefin mixture. In certain embodiments, where (i) the first process fluid comprises ≥90.0 wt. % methanol based on the weight of the first process fluid, (ii) the first portion of the first olefin mixture is a $C_4$ raffinate as specified in the preceding sections, and (iii) the first product and the second olefin mixture are separated from the first reaction mixture by fractional distillation, the second olefin mixture can comprise, e.g., ≤1.0 wt. % methanol, such as 0.05 wt. % to 0.9 wt. % methanol; ≥20.0 wt. % isobutene, such as 30.0 wt. % to 40.0 wt. % isobutene; and ≥50.0 wt. % normal butenes, e.g., 60.0 wt. % to 80.0 wt. % normal butenes, ≥1.0 wt. % of MTBE, and ≤1.0 wt. % of MSBE, and ≤1.0 wt. % of diisobutene, the weight percents being based on the weight of the second olefin mixture.

Referring again to FIG. 1, the second olefin mixture is conducted away from stage S1A via one or more conduits 400, and at least a portion of the second olefin mixture is reacted in second reactor R2. A second process fluid is provided to R2 via one or more conduits 500. The second olefin mixture can be combined with the second process fluid upstream of R2, these being conducted to R2 via one or more conduits 600, as shown. Alternatively, the second olefin mixture and second process fluid can be conducted to R2 via separate conduits, i.e., one or more conduits dedicated to conducting the second olefin mixture and one or more conduits dedicated to conducting the second process fluid.

Figure 2:
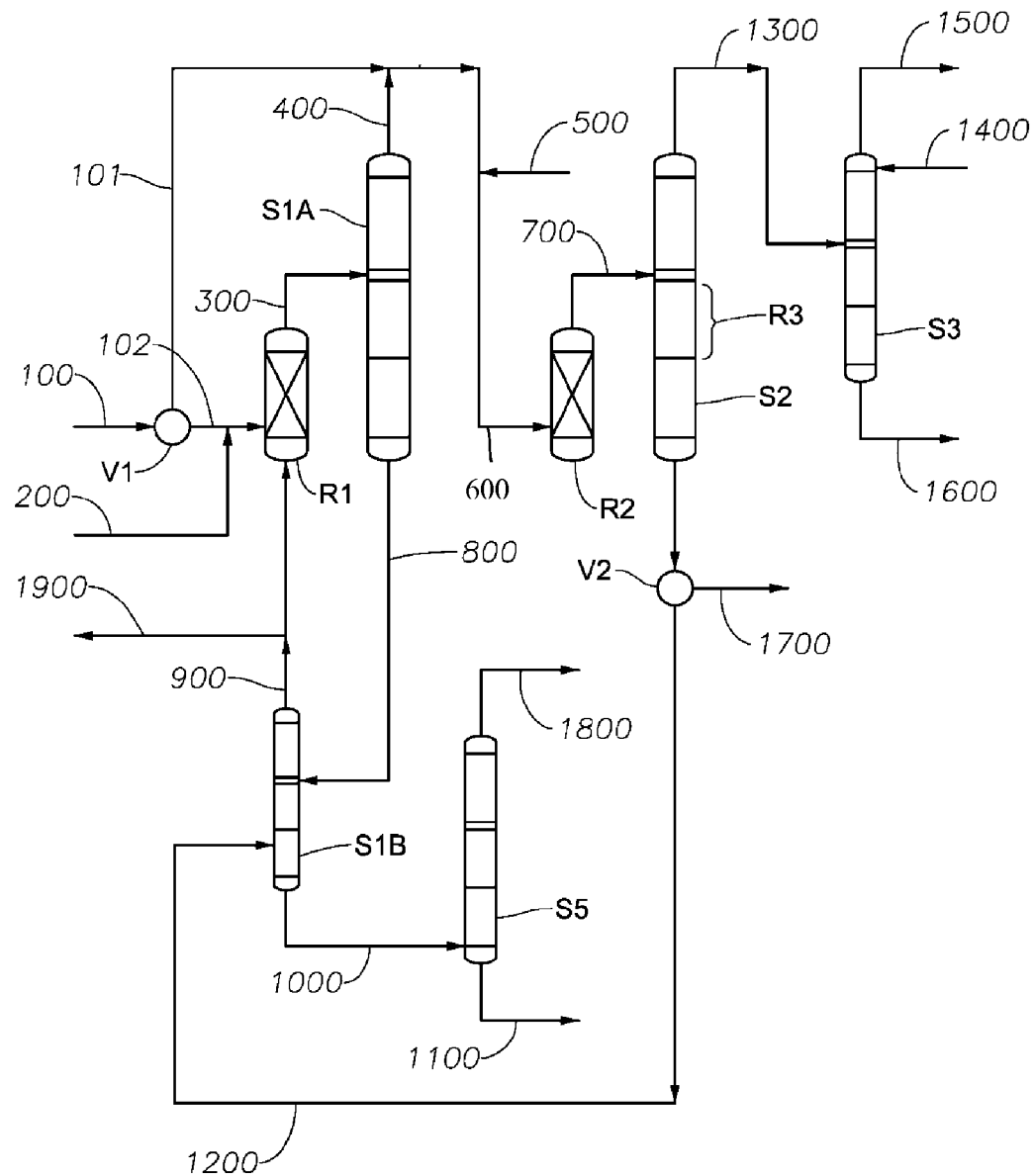
FIG. 2 schematically illustrates a process utilizing the same feed and reactors as that of FIG. 1. The process further comprises (i) separating oxygenates from the first reaction product to produce a first product comprising mono-unsaturated oligomers of order 2 of $C_{3+}$ olefin and (ii) reacting the second reaction mixture in a catalytic distillation reactor to produce a second product comprising oxygenates.

Depending, e.g., on the amount of normal and iso-$C_{3+}$ monoolefin conversion in R1, it can be desirable to increase the amount of $C_{3+}$ monoolefin available for conversion in R2. The additional monoolefin can be, e.g., a the second portion of the first olefin mixture process via one or more conduits 101, as shown in FIGS. 1 and 2. The first and second portions can be obtained from the same source, e.g., by dividing the first olefin mixture into first and second portions, with the first portion being conducted to R1 via conduit 102 and the second portion being conducted to R2 via conduit 101. In certain embodiments, e.g., those shown in FIGS. 1 and 2, valve means V1 are utilized to divert a portion of the first olefin mixture to R2 via conduit 101, with the remainder of the first olefin mixture (the first portion) being conducted to R1 via conduit 102. The mass ratio of the amount of the first olefin mixture conducted to R1 ("first portion"):first olefin mixture conducted to R2 ("second portion") can be, e.g., in the range of from about 0.1 to about 10.0, such as in the range of about 0.2 to about 5.0, or about 0.5 to about 2.0. Valve means, such as V1, can be utilized for directing portions of the source material into conduits 101 (second portion) and 102 (first portion). In the embodiments illustrated in FIGS. 1 and 2, the second portion (conduit 101) is combined with at least a portion of the second olefin mixture from conduit 400 to produce the third olefin mixture. The third olefin mixture is conducted to R2 via one or more conduits 600. The third olefin mixture can be combined with the second process fluid (conduit 500) upstream of R2, as shown, or alternatively, these streams can be provided to R2 via separate conduits. In these representative embodiments, the third olefin mixture can comprise a mixture of at least a portion of the second olefin mixture and the second portion of the first olefin mixture (FIG. 2). Splitting the mixture in this fashion allows for varying the amounts of $C_{4+}$ oxygenate and di-$C_{3+}$ olefins made via the process, e.g. to provide a di-$C_{3+}$ olefin:$C_{4+}$ oxygenate ratio in the range of about 0.01 to about 100, such as about 0.1 to about 10.

In certain embodiments, the third olefin mixture comprises ≥1.0 wt. % of $C_{3+}$ olefin based on the weight of the third olefin mixture, with the third olefin mixture containing (i) the second portion of the first olefin mixture and (ii) at least a portion of the second olefin mixture. In certain embodiments where (i) the first process fluid comprises ≥90.0 wt. % methanol based on the weight of the first process fluid, (ii) the first olefin mixture comprises ≥95.0 wt. % of $C_4$ monoolefins based on the weight of the first olefin mixture, and (iii) the first product and the second olefin mixture are separated from the first reaction mixture by fractional distillation, the third olefin mixture can comprise, e.g., ≤0.1 wt. % methanol; ≥5.0 wt. % isobutene, such as 10.0 wt. % to 20.0 wt. % isobutene; ≥50.0 wt. % normal butenes, such as 80.0 wt. % to 90.0 wt. % normal butenes; ≤1.0 wt. % MTBE; ≤1.0 wt. % MSBE; ≤1.0 wt. % oligomers of order ≥3 of $C_{3+}$ olefin; and ≤1.0 wt. % diisobutene, the weight percents being based on the weight of the third olefin mixture.

The second process fluid generally comprises ≥10.0 wt. % alcohol (e.g., alkyl alcohol) based on the weight of the second process fluid, e.g., ≥50.0 wt. %, such as ≥65.0 wt. %. When the third olefin mixture comprises primarily $C_4$ olefin, the second process fluid generally comprises ≥65.0 wt. % methanol, such as ≥90.0 wt. % methanol, based on the weight of the second process fluid. For example, the second process fluid can comprise ≥60.0 to 70.0 wt. % methanol, 20.0 wt. % to 30.0 wt. % MTBE, and 1.0 wt. % to 10.0 wt. % MSBE, based on the weight of the second process fluid. In such embodiments, the weight ration of third olefin mixture to second process fluid is in the range of 0.5 to 2, e.g., 1 to 1.3.

Second reactor R2 is utilized for reacting the third olefin mixture and the second process fluid to produce the second reaction mixture. In certain embodiments, the third olefin mixture and the second process fluid react in the presence of a catalytically effective amount of a second catalyst, R2 being operated under catalytic conversion conditions. Conventional olefin conversion catalysts and conversion conditions can be utilized, though the invention is not limited thereto. The second catalyst can be selected from among the same catalyst used in R1. In certain embodiments, the second catalyst has substantially the same composition as the first catalyst.

Suitable catalytic conversion conditions for R2 include exposing the catalyst, third olefin mixture and second process fluid to a temperature ≥50.0° C., at a pressure ≥1.0 bar (absolute), and a space velocity (LHSV) ≥1. Operating at temperature conditions different from R1 allows reactor R2 to more effectively convert at least a portion of the $C_{3+}$ olefins into ethers and di-$C_{3+}$ olefins when the concentrations have changed because of reactions and separations occurring in R1 and separated in the intermediate equipment. Because the conditions used in S1A can be altered to direct the ethers and di-$C_{3+}$ olefins into stream 800, the material feeding R2 will have a more favorable equilibrium for making ethers in reactor R2. This requires a smaller reactor with a lower inventory of catalyst than would be required without this separator. When at least one bed of cation exchange resin catalyst is used in R2, the conditions can include (i) an inlet temperature ≥35.0° C., e.g., in the range of 40.0° C. to 50.0° C. (SOR), rising to an inlet temperature in the range of 55.0° C. to 65.0° C. (EOR); (ii) an outlet temperature ≥50.0° C., e.g., in the range of 55.0° C. to 65.0° C. (SOR), rising to an outlet temperature in the range of 70.0° C. to 80.0° C. (EOR); (iii) a pressure ≥1.0 bar (absolute), e.g., in the range of 10 bar to 20 bar, and (iv) a space velocity (LHSV) in the range of 2 to 7.

The reaction in R2 of at least a portion of the $C_{3+}$ olefin of the third olefin mixture with at least a portion of the alcohol of the second process fluid under the specified conditions produces a second reaction mixture comprising ether and having a di-$C_{3+}$ olefin:ether molar ratio <1.0. The second reaction mixture generally further comprises di-$C_{3+}$ olefin, unreacted alcohol, unreacted $C_{3+}$ olefin, and oligomers of order ≥3 of $C_{3+}$ olefin. When (i) the third olefin mixture comprises ≥95.0 wt. % $C_4$ iso-monoolefin (e.g., isobutene) based on the weight of third olefin mixture, (ii) the second process fluid comprises ≥65.0 wt. % methanol, and (iii) the weight ratio of third olefin mixture:second process fluid is in the specified range; then the second reaction mixture generally comprises ≤0.5 wt. % methanol, ≤5.0 wt. % isobutene, ≥50.0 wt. % normal butenes, ≥10.0 wt. % MTBE, ≤1.0 wt. % MSBE, ≤1.0 wt. % oligomers order ≥3 of $C_{3+}$ olefin, and ≤1.0 wt. % diisobutene, wherein the diisobutene:ether molar ratio is <1.0, such as <0.5, or <0.1; the weight percents being based on the weight of the second reaction mixture. For example, the second reaction mixture can comprise 0.05 wt. % to 0.5 wt. % methanol, 5.0 wt. % to 15.0 wt. % isobutene, 70.0 wt. % to 80.0 wt. % normal butenes, 15.0 wt. % to 25.0 wt. % MTBE, 0.05 wt. % to 0.5 wt. % MSBE, ≤1.0 wt. % oligomers of order ≥3 of $C_{3+}$ olefin, and ≤1.0 wt. % diisobutene, the weight percents being based on the weight of the second reaction mixture, wherein the diisobutene:MTBE molar ratio is <0.5, e.g., such as <0.1. The second reaction mixture is conducted away from R2 via one or more conduits 700.

The molar ratio of di-$C_{3+}$ olefin:ether in the first reaction mixture (and in the first product) is greater than the molar ratio of di-$C_{3+}$ olefin:ether in the second product, e.g., ≥5 times greater, such as ≥10 times greater, or even ≥100 times greater. One aspect of the invention relates to regulating olefin feed and/or process conditions in response to changes in the relative need for ether and di-$C_{3+}$ olefin. For example, (i) the relative amount $C_{3+}$ monoolefin conducted to R1 and R2, (ii) the catalyst utilized in R1 and/or R2, (iii) the process conditions utilized in R1 and/or R2, (iv) the amount of $C_{3+}$ monoolefin of the second portion of the first olefin mixture that is added to the second olefin mixture, (v) by adding to R1 at least a portion of the ether (e.g., MTBE) produced by R2 in order to further suppress the amount of ether produced by R1 by shifting chemical equilibrium in favor of di-$C_{3+}$ olefin production, or some combination of (i)-(v) can be utilized to regulate the relative amounts of ether and di-$C_{3+}$ olefin. For example, in response to the relative need for isobutene and/or MTBE for gasoline blending, one or more of factors (i)-(v) can be regulated to adjust the relative amount of these molecules simultaneously produced by the process.

In certain embodiments, the second reaction mixture comprises ≥1.0 wt. % of unreacted third olefin mixture and/or ≥1.0 wt. % of unreacted second process fluid, the weight percents being based on the weight of the second reaction mixture. If desired, at least a portion of the second reaction mixture can be conducted via line 700 to a third reactor R3 for reacting at least a portion of the unreacted second process fluid and/or at least a portion of the unreacted third olefin mixture to produce a third reaction mixture.

The third reactor R3 can comprise one or more stand-alone reactors, or optionally one or more reactor-separators (R3 and S2) as illustrated schematically in FIG. 2. When R3 is a component of a reactor-separator, the reaction conditions and catalyst can be substantially the same as those disclosed in U.S. Pat. No. 4,307,254, which is incorporated by reference herein in its entirety.

As disclosed in U.S. Pat. No. 7,473,812, it can be desirable to operate the reactor-separator R3/S2 under reflux conditions, e.g., by cooling and returning to the reactor-separator a portion of the first byproduct of line 1300. Since it is generally desirable to specify the size of the R3/S2 vessel for operations which produce more di-$C_{3+}$ olefin (conducted away via line 1800) and less (on a molar basis) $C_{4+}$ oxygenate (conducted away via line 1700), it has been found that a greater reflux ratio is needed than is utilized in U.S. Pat. No. 7,473,812. Generally, the reflux ratio (weight basis) is ≥1.55, e.g., ≥1.6, such as ≥1.65, or in the range of about 1.6 to about 2.0, or about 1.70 to 1.90.

In certain embodiments, for example, the reactor-separator comprises a distillation column packed with a supported acid catalyst. When the second reaction mixture comprises $C_4$ monoolefin and methanol, the reactor-separator's reactor functionality produces a third reaction mixture comprising MTBE. The reactor-separator's separation functionality is then utilized to separate from the third reaction mixture (i) a second product (as a bottoms stream) comprising MTBE, and (ii) a first byproduct (as an overhead stream) that is relatively free of isobutene, e.g., comprises ≤1.0 wt. % isobutene based on the weight of the first byproduct. At least a portion of the second product is conducted away from the reactor-separator via one or more conduits 1200. If desired, at least a portion of the second product is conducted away from the process via one or more conduits 1700. The first byproduct can be conducted away from the reactor-separator via one or more lines 1300. Optionally, the second reaction mixture is introduced into the reactor-separator at a location upstream of the reactor-separator's catalyst, with upstream in this instance being with respect to the flow of the third reaction mixture. In other words, the catalyst of the reactor-separator is positioned between (i) the location where the second reaction mixture enters the reactor separator and (ii) the location where the second product exits the reactor separator.

When the reactants in R3 include isobutene and methanol, reaction conditions within the reactor-separator can include, e.g., a pressure in the range of 0 bar (gauge) to about 30 bar (gauge), such as 2 bar (gauge) to 10 bar (gauge), and a temperature in the range of 0° C. to 150° C., such as 10° C. to 100° C. R3 can utilize, e.g., a catalytically effective amount of at least one conventional MTBE conversion catalyst, e.g., at least one cation resin containing at least one sulfonic acid group. These can be produced by, e.g., polymerization or copolymerization of aromatic vinyl compounds followed by sulfonation. The catalyst can be substantially the same as those utilized for R1 and R2. Although the catalyst of the reactor-separator R3/S2 can be located above, at, or below the location where line 700 enters the reactor-separator, a majority of the catalyst, e.g. ≥75.0 wt. % of the catalyst based on the weight of the catalyst in the reactor-separator, can be located above the location where line 700 enters the reactor-separator. For example, ≥90.0 wt. % or even substantially all of the catalyst can be located above the location where line 700 enters the reactor-separator.

When such a catalyst is utilized in a reactor-separator operating under the specified conditions, the third reaction mixture can comprise ether, with at least a first portion of the ether being produced in the reactor-separator (R3 and S2) by reacting the unreacted second process fluid and/or unreacted third olefin mixture. A second portion of the third reaction mixture's ether comprises ether produced in at least one of the first or second reactor and conducted to the third reactor as a component of the second reaction mixture. Generally, the third reaction mixture comprises ≥about 1.0 wt. % ether based on the weight of the third reaction mixture, e.g., in the range of 1.0 wt. % to 5.0 wt. %. Third reaction mixture can have, e.g., a di-$C_{3+}$ olefin:ether molar ratio <0.1 and a non-oligomerized $C_{3+}$ monoolefin:ether molar ratio <10; e.g., a diisobutylene:MTBE molar ratio <0.1 and a $C_4$ monoolefin (isobutene+normal butenes):MTBE molar ratio <10, where the term "non-oligomerized" means olefin that is not oligomerized in R1, R2, or R3.

In certain embodiments, the second reaction mixture comprises 0.05 wt. % to 0.5 wt. % methanol, 1.0 wt. % to 15.0 wt. % isobutene, 70.0 wt. % to 80.0 wt. % normal butenes, 15.0 wt. % to 25.0 wt. % MTBE, 0.05 wt. % to 0.5 wt. % MSBE, ≤1.0 wt. % oligomers of order ≥3 of $C_{3+}$ olefin, and ≤1.0 wt. % diisobutene, the weight percents being based on the weight of the second reaction mixture, and the second reaction mixture's diisobutene:MTBE molar ratio is <0.5, e.g., such as <0.1. In such cases, the third reaction mixture generally comprises ≤5.0 wt. % methanol, e.g., 0.05 wt. % to 0.5 wt. %; ≤1.0 wt. % isobutene, e.g., 0.05 wt. % to 0.5 wt. %; ≥75.0 wt. % normal butenes, e.g., in the range of 85.0 wt. % to 95.0 wt. %; ≥1.0 wt. % MTBE, e.g., in the range of 1.0 wt. % to 5.0 wt. %; ≤0.5 wt. % MSBE, e.g., 0.05 wt. % to 0.5 wt. %; ≤1.0 wt. % oligomers of order ≥3 of $C_{3+}$ olefin, and ≤0.1 wt. % diisobutene; the weight percents being based on the weight of the third reaction mixture.

The reactor-separator (or one or more stand-alone separators S2) can be utilized for separating from the third reaction mixture the second product (conduit 1200) and a first byproduct (conduit 1300); wherein (i) the second product comprises ether, e.g., ≥50.0 wt. % MTBE based on the weight of the second product, such as ≥90.0 wt. % MTBE and (ii) the first byproduct comprises ≥90.0 wt. % $C_4$ non-oligomerized monoolefin based on the weight of the first byproduct, where the term "non-oligomerized" means olefin that is not oligomerized in R1, R2, or R3. For example, when (i) R3 is operated under the specified conditions and (ii) the third reaction mixture comprises 0.05 wt. % to 0.5 wt. % methanol; 0.05 wt. % to 0.5 wt. % isobutene; ≥85.0 wt. % to 95.0 wt. % normal butenes; ≥1.0 wt. % to 5.0 wt. % MTBE; 0.05 wt. % to 0.5 wt. % MSBE; ≤1.0 wt. % oligomers of order ≥3 of $C_{3+}$ olefin; and ≤0.1 wt. % diisobutene; based on the weight of the third reaction mixture, then (a) the second product can comprise ≤1.0 wt. % methanol; ≥75.0 wt. % MTBE, e.g., ≥80.0 wt. %, such as ≥90.0 wt. %; ≤25.0 wt. % MSBE, e.g., ≤20.0 wt. %, such as ≤15.0 wt. %; ≤0.1 wt. % of $C_4$ monoolefin; ≤0.1 wt. % of diisobutene; and ≤0.1 wt. % of oligomers of order ≥3 of $C_{3+}$ olefin; the weight percents being based on the weight of the second product; and (b) the first byproduct can comprise ≥1.0 wt. % methanol; ≥90.0 wt. % of $C_4$ monoolefin; ≤0.1 wt. % of diisobutene; ≤0.1 wt. % of order ≥3 of oligomers of $C_{3+}$ olefin; ≤0.1 wt. % MTBE; and ≤0.1 wt. % MSBE, the weight percents being based on the weight of the first byproduct.

In certain embodiments, a third separation stage S3 can be utilized for separating $C_{3+}$ monoolefin from the first byproduct. For example, a third process fluid can be utilized for extracting alcohol from the first byproduct, the third process fluid comprising ≥50.0 wt. % water based on the weight of the third process fluid. A first raffinate can be conducted away from S3 via one or more conduits 1500, the first raffinate comprising ≥50.0 wt. % non-oligomerized monoolefins based on the weight of the first raffinate, where the term "non-oligomerized" means olefin that is not oligomerized in R1, R2, or R3. The first extract can comprise, e.g., water and ≥90.0 wt. % of the first byproduct's alcohol based on the weight of the first byproduct. The first extract can be conducted away from the S3 via one or more conduits 1600, as shown in FIG. 2.

In certain embodiments, a fourth separation stage (shown schematically as S1B in FIG. 2) is utilized for separating from the first product (i) a second byproduct comprising ether and (ii) a third product comprising di-$C_{3+}$ olefin; the second byproduct having a di-$C_{3+}$ olefin:ether molar ratio ≤0.10 and the third product having oligomers of order 3 of $C_{3+}$ olefin: di-$C_{3+}$ olefin molar ratio ≤1.0. The fourth separation stage can be a stand-alone separation stage, as shown in FIG. 2, or alternatively, it can be a separation zone within first separation stage S1. The second byproduct can be conducted away from S1B via one or more conduits 900, and the third product can be conducted away via one or more conduits 1000. Removing the second byproduct in S1B provides an energy efficiency advantage as well as a material recovery advantage. Ethers utilized for moderation of the reaction in R1 are separated from di-$C_{3+}$ olefins and sent to S1B at a higher temperature than if recovered further downstream. This reduces the energy input into S1B, and also prevents the loss of ethers to the di-$C_{3+}$ olefins product streams. The second product also provides a convenient ether source, e.g., an MTBE source, which can be conducted to R1 for shifting chemical toward di-$C_{3+}$ olefin production and away from the production of oligomer of order ≥3 of $C_{3+}$ olefins.

In certain embodiments, a fifth separation stage S5 can be utilized for separating from the third product a first portion comprising ≥90.0 wt. % di-$C_{3+}$ olefin based on the weight of the first portion and a second portion comprising ≥50.0 wt. % of oligomers of order 3 of $C_{3+}$ olefin ("tri-$C_{3+}$ olefin"), e.g., ≥90.0 wt. % triolefin, based on the weight of the second portion. The first portion of the third product can be conducted away via one or more conduits 1800, and the second portion of the first product can be conducted away via one or more conduits 1100. The first portion can comprise, e.g., ≥90.0 wt. % diisobutylene, based on the weight of the first portion. The second portion can comprise, e.g., ≥50.0 wt. % of oligomers of order 3 of $C_{3+}$ olefins, based on the weight of the second portion.

In certain embodiments, splitter means (e.g., valve means V2) are utilized for separating and conducting away from the process at least a portion of the second product via conduit 1700. A second portion of the second product can be conducted to separators 1B via one or more conduits 1200 for separating ether from the second product. Optionally, at least a portion of the second byproduct is conducted to the first reactor R1 via one or more conduits 900 to lessen the production of ether in the first reactor. Excess MTBE, e.g., an amount substantially beyond that needed for suppression of MTBE production in R1, can be separated from the second byproduct by, e.g., one or more valve means (not shown), and can be conducted away via one or more conduits 1900.

In certain embodiments, (i) the source material is a $C_4$ raffinate produced by steam cracking a heavy oil, as specified in the preceding sections; (ii) the first and second olefin mixtures, have substantially the same composition as the $C_4$ raffinate; (iii) the first and second process fluid comprise ≥90.0 wt. % methanol based on the weight of the process fluid; and (iv) the reactors R1, R2, separators S1A, S1B, S3, S5, and reactor-separator R3+S2 are operated under the conditions specified herein for the conversion of the mixed $C_4$ raffinate to $C_5$ ethers such as primarily MTBE. In such embodiments, the process can further include, e.g., one or more of the following:

(i) the first product comprises ≥20.0 wt. % of the first reaction mixture and the second olefin mixture comprises ≤80.0 wt. % of the first reaction mixture, based on the weight of the first reaction mixture;

(ii) ≥95.0 wt. % of the second olefin mixture is used to produce the third olefin mixture, based on the weight of the second olefin mixture;

(iii) ≥50.0 wt. % of the second byproduct is conducted to the first reactor for the lessening of the ether production in the first reactor;

(iv) the first portion of the third product comprises ≥85.0 wt. % of the third product, and the second portion comprises ≤15.0 wt. % of the third product, the weight percents being based on the weight of the third product; and (v) the first portion of the second product comprises ≥90.0 wt. % of the second product and the second portion of the second product comprises ≤10.0 wt. % of the second product, the weight percents being based on the weight of the second product.

For example, the process can include one or more of (i) the first portion of the second product comprises ≥98.0 wt. % MTBE based on the weight of the first portion, (ii) the first portion of the third product comprises ≥98.0 wt. % diisobutylene based on the weight of the third product, and (iii) at least 75.0 wt. % of the isobutylene in the first and third olefin mixtures is converted to the second product's MTBE on the first portion of the third product's diisobutylene.

In certain embodiments, the invention comprises means for decomposing (e.g., dissociating) ether contained in the second product, e.g., MTBE contained in the first portion of the second product being conducted via conduit 1700 can be dissociated to produce isobutene and methanol. Conventional methods for ether dissociation can be utilized, but the invention is not limited thereto. Suitable ether decomposition methods include those disclosed in U.S. Pat. No. 7,910,786, which is incorporated by reference herein in its entirety, which are particularly suitable when the second product contains a significant amount of MSBE in addition to MTBE. One method for dissociating the second product's ether will now be described in more detail. The invention is not limited to this embodiment, and this description is not meant to foreclose other embodiments within the broader scope of the invention.

In certain embodiments, the second product comprises ≤1.0 wt. % methanol; ≥75.0 wt. % MTBE, e.g., ≥80.0 wt. %, such as ≥90.0 wt. %; ≥0.01 wt. % MSBE, e.g., 0.01 wt. % to 2.0 wt. % MSBE, such as in the range of 0.8 wt. % to 1.5 wt. %; ≥0.01 wt. % tert-amyl methyl ether ("TAME"), e.g., in the range of 0.01 wt. % to 2.0 wt. % TAME, such as in the range of 0.01 wt. % to 1.0 wt. %; and ≥0.01 wt. % $C_{5+}$ olefin, e.g., 0.01 wt. % to 2.0 wt. % $C_{5+}$ olefin, such as in the range of 0.01 wt. % to 0.10 wt. %, the weight percents being based on the weight of the second product. When a portion of such a second product is conducted away from separator S2 via conduit 1700, separation stage S6 can be utilized for separating from the second product (i) an overhead fraction comprising ≥90.0 wt. % of the second product's $C_{4+}$ olefin, based on the weight of the second product's $C_{4+}$ olefin and (ii) a bottoms fraction comprising the remainder of the second product. The bottoms fraction can be conducted away from S6 via one of more conduits 2010. Separation stage S7 can be utilized for separating from the S6 bottoms fraction (i) an overhead fraction comprising ≥90.0 wt. % MTBE based on the weight of the overhead fraction and (ii) a bottoms fraction comprising (a) ≥50.0 wt. % of the second product's TAME and (b) ≥50.0 wt. % of the second product's MSBE. The S6 overhead fraction (conduit 2000) and the S7 bottoms fraction (conduit 2020) can be combined and conducted away from the process, e.g., for blending with gasoline. The S7 overhead fraction can be conducted via one or more conduits 2030 to at least one of reactors R4 or R5, the reactors being utilized for converting the second product's MTBE to a mixture of isobutene and methanol. Generally, one of reactors R4 or R5 is in use while catalyst within the remaining reactor is being regenerated. Valve means (not shown) can be utilized for directing the flow from conduit 2030 into reactor R4 or reactor R5, and for directing the isobutene and methanol into conduit 2040. The catalyst and process conditions utilized in R4 and R5 can be the same as those disclosed in U.S. Pat. No. 7,910,786.

The mixture of isobutene and methanol produced in R4 and/or R5 can be conducted to separation stage S8. A bottoms fraction comprising ≥50.0 wt. % methanol based on the weight of the bottoms fraction can be conducted away from S8 via conduit 2050. An overhead fraction comprising ≥50.0 wt. % isobutene based on the weight of the overhead fraction can be conducted away from S8 via conduit 2060. When the overhead fraction further comprises ≥0.01 wt. % of one or more of di-methyl ether, normal butenes and/or methanol, based on the weight of the overhead fraction, additional separation stages can be utilized from separating at least a portion of one or more of these from the isobutene. For example, S9 can be utilized for extracting methanol utilizing water as an extractant, the water being provided via conduit 2070. A mixture of water and methanol can be conducted away from S9 via conduit 2080, with the methanol being separated and conducted away via conduit 3040 (e.g., for re-use via conduits 200 and/or 500) from separator S11. Water can be conducted away via conduit 3030. When the overhead from S9 comprises the desired isobutene product and further comprises di-methyl ether, the overhead fraction can be conducted via conduit 2090 to separator S10, for separating and conducting away via conduit 3010 at least a portion of the di-methyl ether. The desired isobutene is conducted away via conduit 3000.

Figure 3:
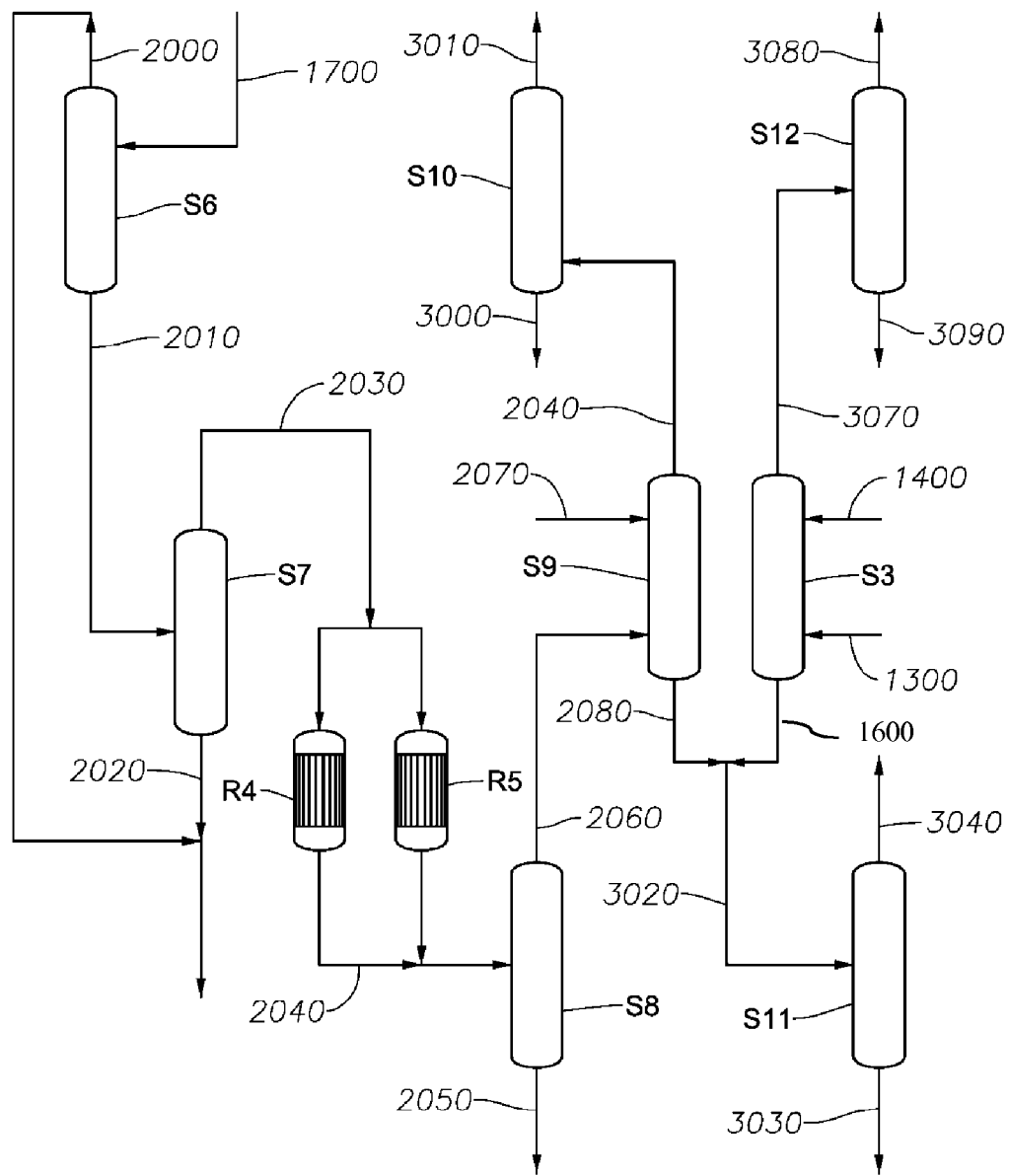
FIG. 3 schematically illustrates a process for decomposing at least a portion of the second product's oxygenates to produce $C_{4+}$ olefins.

In certain embodiments, an overhead fraction comprising $C_{4+}$ olefin and di-methyl ether can be conducted away from S3 (as described in the embodiment of FIG. 2) via line 3070, with separator S12 being utilized to separate at least a portion of the di-methyl ether from the $C_{4+}$ olefin. The $C_{4+}$ olefin can be conducted away from S12 via conduit 3090 for, e.g., polymerization, with at least a portion of the di-methyl ether being conducted away via conduit 3080. The process for simultaneously producing diisobutene and MTBE from a source material comprising a mixture of normal and iso $C_4$ olefin, as illustrated in FIG. 2, can be utilized with the process of FIG. 3 for converting at least a portion of the MTBE to isobutene. In other words, the embodiments of FIGS. 2 and 3 can be used in sequence to separate at least a portion of the source material's isobutene. The relative amount of isobutene separated from the source material is a function of the relative amount of source material converted to MTBE (instead of DIB) in the isobutene conversion reactions illustrated in FIG. 2. The invention thus provides a method for flexibly regulating the relative amounts of isobutene, diisobutene ("DIB"), and MTBE in response to a varying need for these molecules.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including as features which would be treated as equivalents thereof by those skilled in the art to which this disclosure pertains.

When numerical lower limits and numerical upper limits are listed herein, ranges from any lower limit to any upper limit are contemplated. The term "comprising" is synonymous with the term "including". Likewise whenever a composition, as element or a group of components is preceded with the transitional phrase "comprising", it is understood that we also contemplate the same composition or group of components with transitional phrases "consisting essentially of," "consisting of", "selected from the group of consisting of," or "is" preceding the recitation of the composition, component, or components, and vice versa.

What is claimed is:

1. An olefin upgrading method comprising:
   (a) providing a first portion of a first olefin mixture and a first process fluid, the first olefin mixture comprising ≥1.0 wt. % of $C_{3+}$ iso-olefins based on the weight of the first olefin mixture, and the first process fluid comprising ≥10.0 wt. % alcohol based on the weight of the first process fluid;
   (b) reacting the first portion of the first olefin mixture and the first process fluid in a first reactor to produce a first reaction mixture, the first reaction mixture comprising ether and di-$C_{3+}$ olefin and having a di-$C_{3+}$ olefin: ether molar ratio ≥1.0;
   (c) separating from the first reaction mixture a second olefin mixture and a first product, wherein (A) the second olefin mixture comprises at least a portion of any unreacted first olefin mixture present in the first reaction mixture and (B) the first product (i) comprises at least a portion of the first reaction mixture's di-$C_{3+}$ olefin and at least a portion of the first reaction product's ether and (ii) has a di-$C_{3+}$ olefin: ether molar ratio ≥1.0;
   (d) providing a third olefin mixture and a second process fluid, wherein the third olefin mixture comprises (i) a second portion of the first olefin mixture or a fourth olefin mixture, the fourth olefin mixture comprising ≥1.0 wt. % of $C_{3+}$ iso-olefins based on the weight of the fourth olefin mixture, and (ii) at least a portion of the second olefin mixture, and wherein the second process fluid comprises ≥10.0 wt. % alcohol based on the weight of the second process fluid; and
   (e) reacting the third olefin mixture and the second process fluid in a second reactor to produce a second reaction mixture, the second reaction mixture comprising ether and having di-$C_{3+}$ olefin : ether molar ratio <1.0,
   wherein (i) the first olefin mixture comprises ≥50.0 wt. % of $C_4$ monoolefins based on the weight of the first olefin mixture, (ii) the third olefin mixture comprises ≥50.0 wt. % of $C_4$ monoolefins based on the weight of the third olefin mixture, and (iii) the third olefin mixture has a higher $C_{3+}$ monoolefins concentration than the second olefin mixture.

2. The method of claim 1, wherein (i) the first process fluid comprises ≥50.0 wt. % methanol based on the weight of the first process fluid, (ii) the second process fluid comprises ≥50.0 wt. % methanol based on the weight of the second process fluid, and (iii) the third olefin mixture comprises ≥10.0 wt. % of the second olefin mixture and ≥10.0 wt. % of the second portion of the first olefin mixture.

3. The method of claim 1, wherein the reacting of step (b) is carried out in a first reactor, the reacting of step (e) is carried out in a second reactor, and further comprising conducting at least a portion of the second reaction mixture to a third reactor for reacting at least a portion of any unreacted third olefin mixture and at least a portion of any unreacted second process fluid in the presence of the second reaction mixture to produce a third reaction mixture; wherein the third reaction mixture comprises ether and has (i) a di-$C_{3+}$ olefin: ether molar ratio <1.0 and (ii) a non-oligomerized $C_{3+}$ monoolefin : ether molar ratio <10.

4. The method of claim 3, further comprising separating from the third reaction mixture a second product and a first byproduct, the second product comprising ether and the first byproduct comprising alcohol and non-oligomerized monoolefins.

5. The method of claim 3, further comprising separating from the first product (i) a second byproduct comprising ether and (ii) a third product comprising di-$C_{3+}$ olefin; the second byproduct having a di-$C_{3+}$ olefin : ether molar ratio <0.10 and the third product having tri-$C_{3+}$ olefin : di-$C_{3+}$ olefin molar ratio <1.0.

6. The method of claim 5, further comprising separating from the third product a first portion comprising ≥90.0 wt. % di-$C_{3+}$olefin based on the weight of the first portion and a second portion comprising ≥50.0 wt. % oligomer of order 3 of di-$C_{3+}$olefin based on the weight of the second portion.

7. The method of claim 4, wherein the separation of the second olefin mixture and the first product is carried out in a separator 1A, the separation of the third product and the second byproduct is carried out in a separator 1B, the separation of the first byproduct and the second product is carried out in a separator 2, and the third reactor and the separator 2 are each components of a catalytic distillation tower; and further comprising:
conducting away from the process at least a first portion of the second product;
conducting at least a second portion of the second product to separator 1B, for separating ether from the second product; and conducting at least a portion of the second byproduct to the first reactor to lessen the production of ether in the first reactor.

8. The method of claim 4, further comprising (f) providing a third process fluid, the third process fluid comprising ≥50.0 wt. % water based on the weight of the third process fluid and (g) contacting at least a portion of the first byproduct with the third process fluid to separate (i) a first raffinate comprising ≥50.0 wt. % non-oligomerized monoolefins based on the weight of the first raffinate and (ii) a first extract comprising water and ≥90.0 wt. % of the first byproduct's alcohol based on the weight of the first byproduct.

9. The method of claim 2, further comprising producing the first and second portions of the first olefin mixture by dividing the first olefin mixture into the first and second portion using valve means.

10. The method of claim 3, wherein the first olefin mixture comprises ≥90.0 wt. % of $C_4$ monoolefin based on the weight of the first olefin mixture, the third olefin mixture comprises ≥90.0 wt. % of $C_4$ monoolefin based on the weight of the third olefin mixture, the first process fluid comprises ≥65.0 wt. % methanol based on the weight of the first process fluid, the second process fluid comprises ≥65.0 wt. % methanol based on the weight of the second process fluid, the first product's di-$C_{3+}$ olefin comprises ≥90.0 wt. % diisobutylene based on the weight of the first product's di-$C_{3+}$ olefin, the first product's ether comprises ≥90.0 wt. % MTBE based on the weight of the first product's ether, and the first reaction mixture's ether comprising ≥90.0 wt. % MTBE based on the weight of the first reaction mixture's ether.

11. The method of claim 4, wherein (i) the second product comprises ≥90.0 wt. % ether based on the weight of the second product (ii) the ether of the second product comprises ≥90.0 wt. % MTBE based on the weight of the second product's ether, (iii) the first byproduct's alcohol comprises ≥90.0 wt. % methanol based on the weight of the first byproduct's alcohol, and (iv) the first byproduct's non-oligomerized monoolefin comprises ≥90.0 wt. % $C_4$ monoolefin, based on the weight of the first byproduct's monoolefin.

12. The method of claim 5, wherein (i) ≥90.0 wt. % of the second byproduct's ether comprises MTBE based on the weight of the second byproduct's ether and (ii) the third product comprises ≥50.0 wt. % diisobutadiene based on the weight of the third product.

13. The method of claim 6, wherein (i) the first portion of the third product comprises ≥90.0 wt. % diisobutylene based on the weight of the first portion and the second portion of the third product comprises ≥50.0 wt. % of oligomers of order 3 of $C_{3+}$olefin based on the weight of the second portion.

14. The method of claim 6, wherein
(i) the first product comprises ≥20.0 wt. % of the first reaction mixture and the second olefin mixture comprises ≤80.0 wt. % of the first reaction mixture, based on the weight of the first reaction mixture;
(ii) ≥95.0 wt. % of the second olefin mixture is utilized for producing the third olefin mixture, based on the weight of the second olefin mixture;
(iii) ≥50.0 wt. % of the second byproduct is conducted to the first reactor for the lessening of the ether production in the first reactor;
(iv) the first portion of the third product comprises ≥85.0 wt. % of the third product, and the second portion comprises ≤15.0 wt. % of the third product, the weight percents being based on the weight of the third product; and
(v) the first portion of the second product comprises ≥90.0 wt. % of the second product and the second portion of the second product comprises ≤10.0 wt. % of the second product, the weight percents being based on the weight of the second product.

15. The method of claim 14, wherein (i) the first portion of the second product comprises ≥98.0 wt. % MTBE based on the weight of the first portion, (ii) the first portion of the third product comprises ≥98.0 wt. % diisobutylene based on the weight of the third product, and (iii) at least 75.0 wt. % of the isobutylene in the first and third olefin mixtures is converted to the second product's MTBE.

16. The method of claim 3, wherein the reacting of step (b) is carried out in the presence of a catalyst comprising ≥95.0 wt. % of at least one cation exchange resin based on the weight of the catalyst; the reacting of step (b) being carried out under conditions including (i) exposing the catalyst, first olefin mixture and first process fluid to a temperature ≥50.0° C., (ii) a pressure ≥1.0 bar (absolute), and (iii) a space velocity (LHSV) ≥1.0.

17. The method of claim 3, wherein the reacting of step (e) is carried out in the presence of a second catalyst, the second catalyst comprising ≥95.0 wt. % of at least one cation exchange resin based on the weight of the second catalyst; the reacting of step (e) being carried out under conditions including exposing the second catalyst, the third olefin mixture and the second process fluid to an inlet temperature ≥35.0° C. and a pressure in the range of 10 bar to 20 bar (absolute).

18. The method of claim 3, wherein the third reactor is operated under conditions including exposing the second reaction mixture to a pressure in the range of 2 bar (gauge) to 10 bar (gauge) and a temperature in the range of 10° C. to 100° C. in the presence of a third catalyst.

19. The method of claim 4, further comprising decomposing in a fourth reactor at least a portion of the second product to produce a decomposition mixture comprising alkyl alcohol and ≥90.0 wt. % iso-$C_{4+}$ mono olefin, based on the weight of the decomposition mixture's olefin.

20. The method of claim 19, wherein the decomposition mixture's iso-$C_{4+}$ mono olefin comprises ≥90.0 wt. % isobutene and the decomposition mixture's alkyl alcohol comprises ≥90.0 wt. % methanol.

21. The method of claim 20, wherein (i) 10.0 wt. % to 90.0 wt. % of the first olefin mixture's isobutylene is converted to MTBE in at least one of the first, second, or third reactors, and (ii) 10.0 wt. % to 90.0 wt. % of the MTBE is decomposed in the fourth reactor to produce the decomposition mixture.

22. The method of claim 21, further comprising separating at least a portion of the decomposition mixture's isobutene.

23. The method of claim 22, further comprising polymerizing at least a portion of the separated isobutene.

24. An olefin upgrading method comprising:
(a) providing a first olefin mixture and a first process fluid, the first olefin mixture comprising ≥0.1 wt. % of $C_{3+}$ olefins based on the weight of the first olefin mixture, and the first process fluid comprising ≥10.0 wt. % alcohol based on the weight of the first process fluid;
(b) reacting a first portion of the first olefin mixture and the first process fluid in a first reactor to produce a first reaction mixture, the first reaction mixture comprising ether and di-$C_{3+}$ olefin and having a di-$C_{3+}$ olefin : ether molar ratio ≥1.0;
(c) separating from the first reaction mixture a second olefin mixture and a first product, wherein (A) the second olefin mixture comprises at least a portion of any unreacted first olefin mixture present in the first reaction mixture and (B) the first product (i) comprises at least a portion of the first reaction mixture's di-$C_{3+}$ olefin and at least a portion of the first reaction mixture's ether and (ii) has a di-$C_{3+}$ olefin : ether molar ratio ≥1.0;
(d) providing a third olefin mixture and a second process fluid, the third olefin mixture comprising (i) a second portion of the first olefin mixture and (ii) at least a portion of the second olefin mixture, and the second process fluid comprising ≥10.0 wt. % alcohol based on the weight of the second process fluid;
(e) reacting the third olefin mixture and the second process fluid in a second reactor to produce a second reaction mixture, the second reaction mixture comprising ether and having di-$C_{3+}$ olefin:ether molar ratio <1.0; and
(f) conducting at least a portion of the second reaction mixture to a third reactor for reacting at least a portion of any unreacted third olefin mixture and at least a portion of any unreacted second process fluid in the presence of the second reaction mixture to produce a third reaction mixture; wherein the third reaction mixture comprises ether and has (i) a di-$C_{3+}$ olefin:ether molar ratio <1.0 and a monoolefin : ether molar ratio <0.10, wherein (i) the first olefin mixture comprises ≥50.0 wt. % of $C_4$ monoolefins based on the weight of the first olefin mixture, (ii) the third olefin mixture comprises ≥50.0 wt. % of $C_4$ monoolefins based on the weight of the third olefin mixture, and (iii) the third olefin mixture has a higher $C_{3+}$ monoolefins concentration than the second olefin mixture.

25. The method of claim 24, further comprising (i) separating from the third reaction mixture a second product and a first byproduct, the second product comprising ether and the first byproduct comprising alcohol and monoolefins, and (ii) decomposing at least a portion of the second product's ether to produce a decomposition mixture comprising alkyl alcohol and ≥90.0 wt. % iso-$C_{4+}$ monoolefin, based on the weight of the decomposition mixture's olefin.

* * * * *